(12) United States Patent
Shen et al.

(10) Patent No.: US 6,727,381 B2
(45) Date of Patent: Apr. 27, 2004

(54) PROCESS FOR PRODUCING VITAMIN A ESTER

(75) Inventors: Runpu Shen, Zhejiang (CN); Shiqing Pi, Zhejiang (CN); Bin Xie, Zhejiang (CN); Hongjun Huang, Zhejiang (CN)

(73) Assignee: Zhejiang Medicine Co., Ltd., Xinchang Pharmaceutical Factory, Zhejiang (CN)

( * ) Notice: Subject to any disclaimer, the term of this patent is extended or adjusted under 35 U.S.C. 154(b) by 0 days.

(21) Appl. No.: 10/039,056

(22) Filed: Jan. 3, 2002

(65) Prior Publication Data
US 2002/0151742 A1 Oct. 17, 2002

(30) Foreign Application Priority Data
Jan. 5, 2001 (CN) .......................... 01105024 A

(51) Int. Cl.[7] .............................................. C07C 67/02
(52) U.S. Cl. ........................................................ 560/260
(58) Field of Search ............................................ 560/260

(56) References Cited

U.S. PATENT DOCUMENTS

| | | | |
|---|---|---|---|
| 3,708,306 A | * 1/1973 | Appleman ........................ 99/2 |
| 4,916,250 A | 4/1990 | Babler ............................ 558/217 |
| 5,043,356 A | * 8/1991 | Fulton, Jr. ....................... 514/549 |
| 5,424,478 A | 6/1995 | Tanaka et al. .................. 560/260 |
| 5,527,952 A | 6/1996 | Kuroda et al. ................. 560/262 |

FOREIGN PATENT DOCUMENTS

CN 1097414 A 1/1995

OTHER PUBLICATIONS

Babler and Schlidt, "An Expedient Route to a Versatile Intermediate for the Stereoselective Synthesis of all–trans–Retinoic Acid and beta–Carotene" Tetrahedron Letters, vol. 33(50), pp. 7697–7700, (1992).*

English translation of abstract and claim 1 of Chinese patent No. 1097414, one page (1995).

Babler, J.H. et al. (1979). "Facile Synthesis of 4–Acetoxy–2–methyl–2–butenal, a Vitamin A Precursor, from Isoprene Chlorohydrin," *J. Org. Chem.* 44(10):1716–1717.

Eletti–Bianchi, G. et al. (1976). "A Two–Step Synthesis of (E)–4–Chloro–2–methylcrotonaldehyde from Isoprene, An Unprecedented Oxidative Chlorination of a 1,3–Diene Monoepoxide by Cupric Chloride," *J. Org. Chem.* 41(9):1648–1650.

Reif, W. and Grassner, H. (Jan. 1973). "Die technische Vitamin–A–Synthese der BASF," *Chemie–Ingieur Technik* 45(10a):646–652b with English translation of relevant portion of the article corresponding to pp. 648 and 650.

Wehrli, P.A. and Schaer, B. (1977). "Nitroacetoxylation of Isoprene," *J. Org. Chem.* 42(17):2939–2940.

* cited by examiner

Primary Examiner—Richard L. Raymond
Assistant Examiner—Zachary C. Tucker
(74) Attorney, Agent, or Firm—Morrison & Foerster LLP

(57) ABSTRACT

The invention relates to a process for producing all trans-vitamin A ester (I). According to the present invention, vitamin A ester (I) can simply be synthesized in good yields and high purity by the reaction of phosphonate compound (IV) with aldehyde (II) in an organic solvent in the presence of a base.

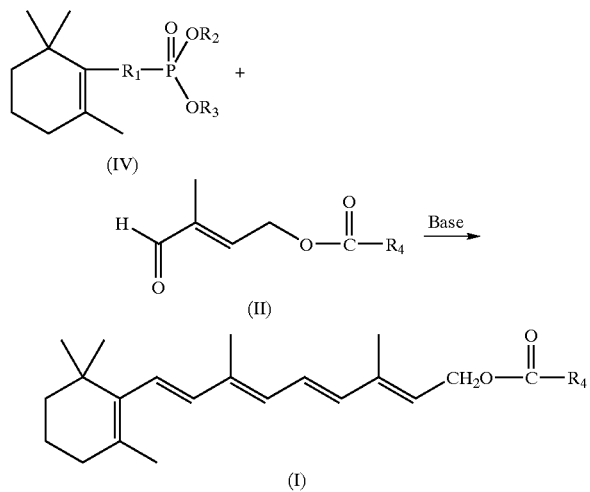

20 Claims, No Drawings

PROCESS FOR PRODUCING VITAMIN A ESTER

The present invention relates to a novel process for producing vitamin A ester and especially to a process for producing all trans-vitamin A ester.

Vitamin A is a known compound. Its chemical formula is represented as following:

[Structure of Vitamin A]

Vitamin A (I)

[Structure of Vitamin A ester]

Vitamin A ester

Vitamin A ester of formula (I) such as, acetate or palmitate are used in great quantities as medicines, food additives and feed additives, etc. A variety of methods for the synthesis of vitamin A and its derivatives have been proposed.

Among those methods, there are three routines relating to Wittig or Wittig-Homer reaction:

[Structure with PPh₃X⁻]

(CN 1097414A)

[Structure of aldehyde with OAc] —Base→

[Structure of product with OAc] + Ph₃PO

[Structure with P(OC₂H₅)₂]

(U.S. Pat. No. 4961250)

[Structure of aldehyde with COOCH₃] —Base→

[Structure of product with COOCH₃] +

[Structure: ⁻O—P(OC₂H₅)₂]

[Structure (III)]

(III)
(CN 1097414A)

[Structure of aldehyde (II)] —Base→

(II)

[Structure of Vitamin A ester (I)]

Vitamin A ester
(I)

The disadvantage of routine 1 lies in the fact that the triphenylphosphine reactant required for the synthesis is relatively expensive and that the byproduct of the reaction, i.e., $Ph_3PO$, is water insoluble, thus it is difficult to isolate the desired product. In routine 2, Wittig-Horner reaction is employed to overcome the shortages existing in routine 1, the byproduct phosphonate is soluble in water, and thus can easily be isolated from desired product. However, the expected product is retinoic acid ester rather than vitamin A ester. In routine 3, intermediate aldehyde (II) in routine 1 and intermediate phosphonate compound (III) in routine 2 were employed to synthesize vitamin A ester directly.

The phosphonate compound (III) can be obtained by the following reactions: (see U.S. Pat. No. 4,916,4250)

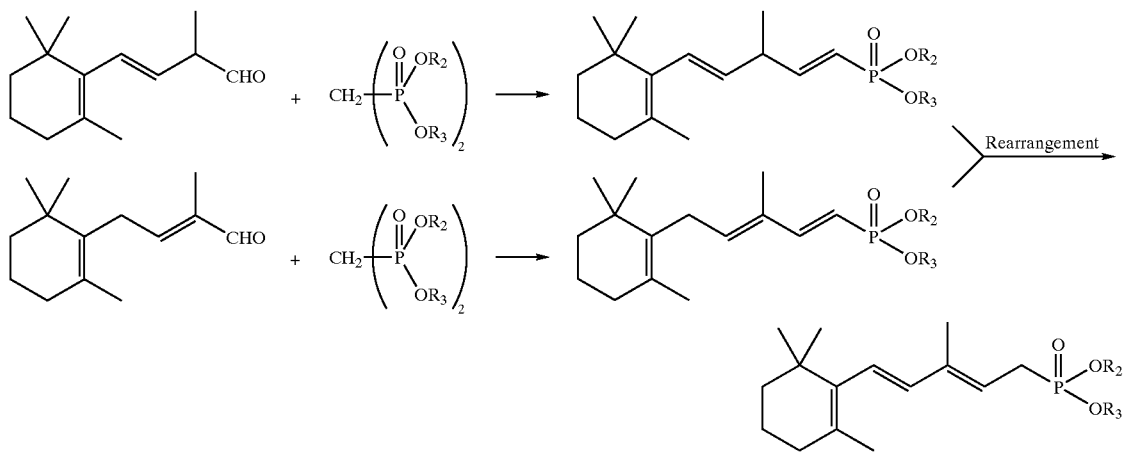

Starting from routine 3, it is an object of this invention to provide an improved process for more conveniently producing vitamin A ester, especially all trans-vitamin A ester in good yields. The advantages of this invention will become apparent from the following descriptions.

This object can be reached by a process for preparation of vitamin A ester, especially all trans-vitamin A ester of formula (I) which comprises treating compound represented by the formula (IV) with aldehyde represented by the formula (II) in an organic solvent in the presence of a base.

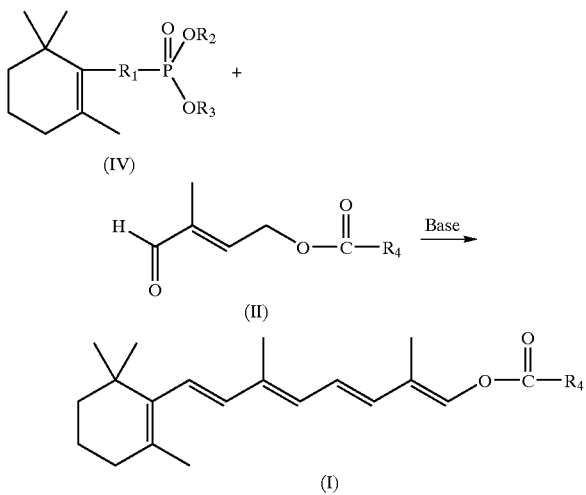

wherein $R_1$=3-methyl-1,3-pentadienyl or 3-methyl-1, 4-pentadienyl, $R_2$ and $R_3$ are identical or different and are $C_1$–$C_4$-alkyl
$R_4$ is $C_1$–$C_{15}$-hydrocarbyl.
Compound (IV) includes:
A; 3-methyl-5-(2, 6, 6-trimethyl-1-cyclohexen-1-yl)-1, 3-pentadienyl-phosphonic acid dialkyl ester B: 3-methyl-5(2, 6, 6-trimethyl-1-cyclohexen-1-yl)-1, 4-pentadienyl-phosphonic acid dialkyl ester or C: the mixture of A and B in any ratios In CN 1097414A, compound (III), which was employed as starting material to synthesize vitamin A ester, was obtained by isomerization of compound (IV). However, according to the present invention, compound (IV) is directly employed as starting material to synthesize vitamin A ester. Due to the omission of isomerization step, vitamin A ester can be prepared in a more simply manner and higher yield according to the process of tie present invention, In present invention, $R_2$ and $R_3$ are identical or different and represent $C_1$–$C_4$ alkyl, for example methyl, ethyl, n-propyl, isopropyl, n-butyl, iso-butyl, sec-butyl and tert-butyl, preferably methyl, ethyl, isopropyl. $R_4$ represents saturated or unsaturated $C_1$–$C_{15}$ hydrocarbyl, for example, alkyl, alkenyl etc., preferably $C_1$–$C_{15}$ alkyl, for example, $C_1$–$C_4$-alkyl as mentioned above, pentyl, hexyl, heptyl, octyl, nonyl, decyl, undecyl, dodecyl, tridecyl, tetradecyl, pentadecyl and the isomer thereof, especially preferably methyl, ethyl, pentadecyl.

It is believed that the mechanism of this reaction is as follows:

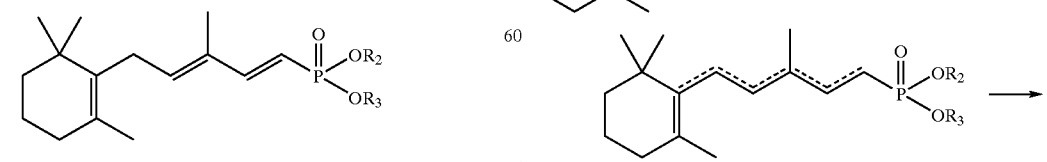

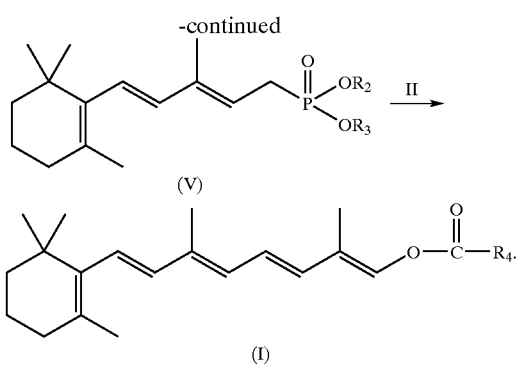

(V)

(I)

According to the process of this invention, vitamin A ester can be obtained by the reaction of compound (II) with intermediate carbanion (V), which is generated when compound (IV) is treated with a proper base. Suitable base is inorganic base or organic base. Preferred inorganic base includes, for example, alkali metal hydrides such as sodium hydride and potassium hydride. Preferred organic base includes organic base of alkali metal, for example, alkali metal alkoxides such as sodium tert-butoxide alkali potassium tert-butoxide, alkali metal salt of sulfoxides such as dimsyl sodium and dimsyl potassium, organolithium compounds such as methyllithium and n-butyllithium; organomagnesium halides such as ethylmagnesium chloride.

The amount of the base is not critical, the molar ratio of base to the compound of formula (IV) is generally from about 1 to about 3, preferably from about 1 to about 2. The molar ratio of the compound of formula (II) to the compound of formula (IV) is generally from about 1 to about 2.

In general, the reaction is carried out in an organic solvent. Any organic solvents which do not adversely affect the reaction can be employed. Preferred organic solvents include two types of organic solvents: (1) nonpolar aprotic solvents, for example, hydrocarbons such as benzene, hexane, cyclohexane, toluene; ethers such as tetrahydrofuran, diisopropyl ether; (2) polar aprotic solvents, for example, sulfoxides such as DMSO, ketones such as acetone, nitrites such as acetonitrile, amides such as DMF, HMPT. These solvents may be used either singly or in combination. Preferably, two types of solvents are used in combination. The amount of the solvent is not critical. Generally, it is advantageous that from about 0.05 to about 1 mole, preferably from about 0.1 to about 0.5 mole of compound (IV) are employed per liter of solvent. The temperature at which the reaction is carried out may be varied in wide rang upon the type of the used base. Generally, the suitable temperature is from about –70° C. to about 70° C., preferably from about –70° C. to about 0° C. The reaction is preferably carried out in an atmosphere of an inert gas such as helium, nitrogen or argon The time of reaction is not critical, generally from 30 minutes to 5 hours, preferably from 2 to 4 hours. Preferably, compound (IV) and base are added in the solvent prior to compound (II).

By the aforesaid reaction, vitamin A ester predominantly containing all trans-vitamin A is formed in good yields from the compound of formula (IV).

The resulting vitamin A ester of formula (I) can be isolated and separated from the reaction mixture in a known manner. For example, water or an aqueous solution of ammonium chloride etc., is added to the reaction mixture, and the organic phase is separated from the mixture. If necessary, the organic phase is washed with water and dried over anhydrous sodium sulfate, and the solvent is evaporated under reduced pressure to separate vitamin A ester. If necessary, the product may be purified, for example, by recrystallization to give vitamin A ester of high purity.

According to the present invention, all trans-vitamin A derivatives can be obtained in good yields and high purity, the content of other isomers such as 9-cis, 11-cis, and 13-cis isomers is very low. It is easy to obtain all trans-vitamin A derivatives from the formed product by conventional purifying means such as recrystallization, Compound of formula (IV) can easily be obtained according to known methods or in analogy to the known methods, for example, it can be obtained from starting material β-ionone according to the method described in U.S. Pat. No. 4,916,250,

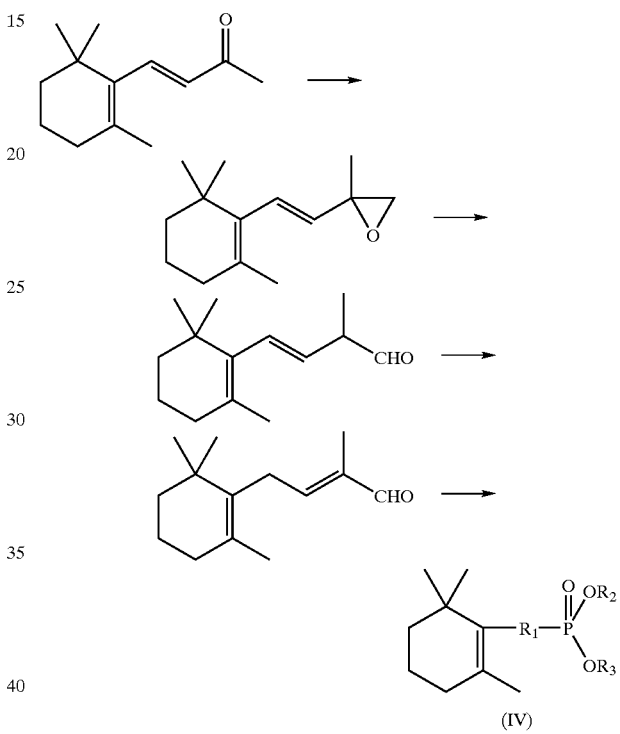

(IV)

As to the synthesis of compound of formula (II), reference is made to, for example, Reif W. et al., Chemie. Ing. Techn, 1973; 45 (10a); 648;

Eletti-Bianchi G. et al., J. Org. Chem. 1976; Vol. 41: 1648;

J. Org. Chem, Vol. 42, 1977, 2939;

U.S. Pat. No. 5,527,952;

J. Org. Chem. Vol, 44, 1979, 1716

EXAMPLES

Example 1

Preparation of Vitamin A Acetate

Under a nitrogen gas atmosphere, a 250 ml brown flask was charged with a solution of 10.0 g (27.4 mmol, 93.2% in purity) of 3-methyl-5-(2, 6, 6,-trimethyl-cyclohexen-1-yl)-1,3-pentadienylphosphonic acid diethyl ester in 40 ml of toluene, cooled to –35° C. Then, a solution of 5.0 g (52 mmol) sodium tert-butoxide in the mixture of 20 ml of DMF and 10 ml of toluene was added dropwise slowly over a period of 10 minutes, and the mixture was stirred successively at the same temperature for 2 hours. A solution of 5.0 g (35.2 mmol) 4-acetoxy-2-methyl-2-butenal in 40 ml of toluene was added dropwise to the solution at −35° C., and the mixture was stirred at this temperature for 10 minutes. 50 ml of water was added to the reaction mixture, the organic phase was separated and washed with 50 ml of saturated brine, dried over anhydrous magnesium sulfate. Removal of the solvent by evaporation under reduced pressure gave 11.0 g of yellow oil.

The yellow oil was analyzed by high performance liquid chromatography (HPLC) under the following conditions:

Column: Nuclesosil 50–54.6×250 mm

Eluent: cyclohexane-diethyl ether 50:1 (v/v)

Flowing Rate: 0.80 ml/min

Detection: UV310 nm

The analysis results showed the content of all trans-vitamin A acetate was 90.3%, the total content of 11-cis and 13 cis isomers was 5.4% and the content of 9-cis isomer was 1.0%.

20 ml of methanol was added to the obtained oil, cooled to −20° C., then stirred for 30 minutes, the crystal was isolated by filtration, dried under reduced pressure. This gave 8.3 g yellow crystal. Analysis of this product according to the analysis method of vitamin A in Chinese Pharmacopeia published in the year of 2000 demonstrated the content of vitamin A of this product was 2680000 unit.

Example 2

Preparation of Vitamin A Acetate

Under a nitrogen gas atmosphere, a 250 ml brown flask was charged with a solution of 10.0 g (27.4 mmol, 93.5% in purity) of 3-methyl-5-(2, 6, 6-trimethyl-cyclohexen-1-yl)-1, 4-pentadienylphosphonic acid diethyl ester in 40 ml of tetrahydrofuran, cooled to −45° C. Then, with stirring, a solution of 4.0 g (35.7 mmol) of potassium tert-butoxide in the mixture of 20 ml of DMF and 20 ml of TBF was added dropwise slowly at the same temperature over a period of 20 minutes, 2 hours later, a solution of 50 g (35.2 mmol) 4-acetoxy-2-methyl-2-butenal in 40 ml of THF was added dropwise to the solution at −45° C. Successively, the mixture was stirred at this temperature for 10 minutes. Then 150 ml of water and 200 ml of petroleum ether was added to the reaction mixture, the organic phase was separated and washed with 100 ml of saturated aqueous solution of sodium chloride, dried over anhydrous magnesium sulfate. Removal of the solvent by evaporation under reduced pressure gave 10.5 g of yellow oil.

In the same way as in example 1, the resulting vitamin A acetate was quantified by HPLC, the content of all trans-vitamin A acetate was 85.0%, the total content of 11-cis and 13-cis isomers was 7.1% and the content of 9-cis isomer was 1.3%.

Example 3

Preparation of Vitamin A Acetate

Under a nitrogen gas atmosphere, a 250 ml brown flask was charged with the mixture of 5.0 g (93.2% in purity) of 3-methyl-5-(2, 6, 6-trimethyl-1-cyclohexen-1-yl)-1, 3-pentadienylphosphonic acid diethyl ester and 5.0 g (93.5% in purity) of 3-methyl-5(2, 6, 6-trimethyl-1-cyclohexen-1-yl)-1, 4-pentadienylphosphonic acid diethyl ester dissolved in 40 ml of toluene, cooled to −35° C. Then, with stirring, a solution of 50 g sodium tert-butoxide in the mixture of 20 ml of DMF and 10 ml of toluene was added dropwise slowly at the same temperature over a period of about 30 minutes, and the mixture was stirred for further 2 hours. A solution of 5.0 g 4-acetoxy-2-methyl-2-butenal in 40 ml of toluene was added dropwise to the stirred mixture with the temperature being maintained at −35° C. After addition was completed, the mixture was stirred at the same temperature for further 10 minutes. Then 100 ml of water was added to the reaction mixture, the organic phase was separated and washed with 50 ml of saturated aqueous solution of sodium chloride, dried over anhydrous magnesium sulfate. Removal of the solvent by evaporation under reduced pressure gave 11.0 g of yellow oil.

In the same way as in example 1, the resulting vitamin A acetate was quantified by HPLC, the content of all trans-vitamin A acetate was 89.2%, the total content of 11-cis and 13-cis isomers was 6.7% and the content of 9-cis isomer was 1.0%

Example 4

Preparation of Vitamin A Propionate

The same reaction and separation as in example 1 were carried out except that 5.6 g (35.8 mmol) 4-propionyloxy-2-methyl-2-butenal instead of 4-acetoxy-2-methyl-2-butenal was used. As a result, 11.5 g of yellow oil was obtained. In the same way as in example 1, the resulting vitamin A: propionate was quantified by UPLC It was found that the content of all trans-vitamin A propionate was 82.5%, the total content of 11-cis and 13-cis isomers was 4.4% and the content of 9-cis isomer was 1.0%.

Example 5

Preparation of Vitamin A Palmitate

Under a nitrogen gas atmosphere, a 250 ml brown flask was charged with a solution of 10.0 g (27.4 mmol, 93.2% in purity) 3-methyl-5-(2, 6, 6-trimethyl-1-cyclohexen-1-yl)-1, 4-pentadienylphosphonic acid diethyl ester in 40 ml of toluene, cooled to −45 C. Then, a solution of 5.0 g (52 mmol) sodium tert-butoxide in 20 ml of DMF was added dropwise slowly over a period of 10 minutes, and the mixture was stirred, at the same temperature for 2 hours. At the same temperature a solution of 12.0 g (36.2 mmol) 4-palmitoyloxy-2-methyl-2-butenal dissolved in 40 ml of toluene was added dropwise slowly to the solution. Then the mixture was stirred at this temperature for further 20 minutes. 60 ml of water was added to the reaction mixture, the organic phase was separated and washed with 60 ml of saturated brine, dried over anhydrous magnesium sulfate. Removal of the solvent by evaporation at reduced pressure gave 14.5 g of yellow oil.

HPLC analysis revealed the content of all trans-vitamin A palmitate was 85.0%, recrystallization in 50 ml mixture of acetone/methatnol (9:1) gave yellow crystal. The content of all trans-vitamin A palmitate was 93.0% by HPLC.

What is claimed is:

1. A process for producing vitamin A ester comprising reacting as starting material a compound represented by the formula (IV) with a compound represented by the formula (II) in an organic solvent in the presence of a base,

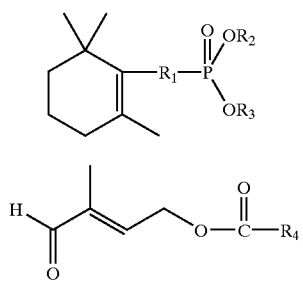

(IV)

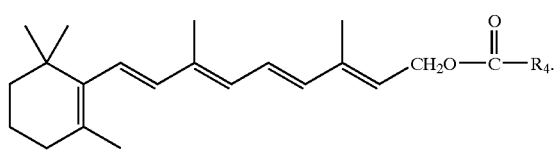

(II)

wherein $R_1$ is 3-methyl-1,3-pentadienyl or 3-methyl-1,4-pentadienyl; $R_2$ and $R_3$ are identical or different and are $C_1$–$C_4$-alkyl; $R_4$ is $C_1$–$C_{15}$-hydrocarbyl.

2. The process of claim 1, wherein the compound (IV) includes
- A: 3-methyl-5-(2, 6, 6-trimethyl-1-cyclohexen-1-yl)-1, 3-pentadienyl-phosphonic acid dialkyl ester,
- B: 3-methyl-5-(2, 6, 6-trimethyl-1-cyclohexen-1-yl )-1, 4-pentadienyl-phosphonic acid diallcyl ester or
- C: the mixture of A and B in any ratios.

3. The process of claim 1, wherein the compound (IV) and base are added in the solvent prior to compound (II).

4. The process of claim 1, wherein $R_4$ is $C_1$–$C_{15}$-alkyl.

5. The process of claim 1, wherein $R_4$ is methyl.

6. The process of claim 1, wherein $R_4$ is ethyl.

7. The process of claim 1, wherein $R_4$ is pentadecyl.

8. The process of claim 1, wherein the vitamin A ester is all trans-vitamin A ester of formula (I)

(I)

9. The process of claim 1, wherein the base is selected from the group consisting of alkali metal hydride, organic base of alkali metal and organomagesium halides.

10. The process of claim 9, wherein the organic base of alkali metal is selected from the group consisting of alkali metal salt of sulfoxides, alkali metal alkoxides and organolithium compounds.

11. The process of claim 1, wherein the organic solvent is selected from the group consisting of a nonpolar aprotic solvent, a polar aprotic solvent, and a mixture of a nonpolar aprotic solvent and a polar aprotic solvent.

12. The process of claim 1, wherein the molar ratio of the compound represented by the formula (II) to the compound represented by the formula (IV) is from about 1 to about 2.

13. The process of claim 1, wherein the molar ratio of the base to the compound represented by the formula (IV) is from about 1 to about 3.

14. The process of claim 1, wherein the reaction is carried out at a temperature of from −70° C. to 70° C.

15. The process of claim 1, wherein the reaction is carried out at a temperature of from −70° C. to 0° C.

16. The process of claim 11, wherein the nonpolar aprotic solvent is a hydrocarbon or an ether.

17. The process of claim 11, wherein the polar aprotic solvent is a sulfoxide, a nitrile, a ketone, or an amide.

18. The process of claim 1, wherein the organic solvent comprises toluene.

19. The process of claim 1, wherein the organic solvent comprises tetrahydrofuran.

20. The process of claim 1, wherein the organic solvent comprises DMF.

* * * * *